United States Patent
De Plater et al.

(10) Patent No.: US 8,206,278 B2
(45) Date of Patent: Jun. 26, 2012

(54) WRAP FOR A HEART ASSIST DEVICE

(75) Inventors: Gemma De Plater, Albert Park (AU); Scott Hugh Miller, Narrabeen (AU)

(73) Assignee: Sunshine Heart Pty Ltd., St. Leonards, NSW (AU)

( * ) Notice: Subject to any disclaimer, the term of this patent is extended or adjusted under 35 U.S.C. 154(b) by 200 days.

(21) Appl. No.: 12/438,105

(22) PCT Filed: Aug. 20, 2007

(86) PCT No.: PCT/AU2007/001188
§ 371 (c)(1),
(2), (4) Date: May 25, 2010

(87) PCT Pub. No.: WO2008/022379
PCT Pub. Date: Feb. 28, 2008

(65) Prior Publication Data
US 2010/0292528 A1   Nov. 18, 2010

(30) Foreign Application Priority Data
Aug. 21, 2006 (AU) .................. 2006904548

(51) Int. Cl.
*A61N 1/362* (2006.01)
(52) U.S. Cl. .............................................. 600/16
(58) Field of Classification Search .............. 600/16
See application file for complete search history.

(56) References Cited

U.S. PATENT DOCUMENTS

| | | |
|---|---|---|
| 283,660 A | 8/1883 | Reed |
| 929,571 A | 7/1909 | Dubied |
| 1,576,397 A | 7/1925 | Yanagi |
| 1,719,316 A | 7/1929 | Appleton |
| 3,467,077 A | 9/1969 | Cohen |

(Continued)

FOREIGN PATENT DOCUMENTS

AU   2003277983   6/2008

(Continued)

OTHER PUBLICATIONS

Seymour Furman et al., "Cardiac Support by Periaortic Diastolic Augmentation", New York Journal of Medicine, Aug. 1, 1970, pp. 1964-1969.

(Continued)

*Primary Examiner* — George Manuel
(74) *Attorney, Agent, or Firm* — Sean D. Solberg

(57) ABSTRACT

A heart assist device in which an inflatable balloon or chamber is held against an outside surface of a curved arterial vessel by a wrap (20) formed from a flexible sheet-like material. The wrap (20) having a first end portion (22), a second end portion (30) and an intermediate portion (26) connecting together the first and second end portions (22, 30). The intermediate portion (26) comprising at least three separate elongate sections (26a-c) arranged in side by side array each connected at each end to a respective one of the end portions (22, 30) of the wrap (20). The improvement in that the laterally outer ones (26a,b) of the elongate sections are longer than the central one (26c) of them. As a result, if the wrap (20) was laid on a planar surface, the central (26c) one of the elongate sections would lie substantially in that plane and the laterally outer ones (26a,b) of the elongate sections would, intermediate their ends, project above that plane.

11 Claims, 8 Drawing Sheets

U.S. PATENT DOCUMENTS

| | | | |
|---|---|---|---|
| 3,552,383 A | 1/1971 | Krueger et al. | |
| 3,597,766 A | 8/1971 | Buck | |
| 4,014,318 A | 3/1977 | Dockum et al. | |
| 4,051,840 A | 10/1977 | Kantrowitz et al. | |
| 4,176,411 A | 12/1979 | Runge | |
| 4,195,623 A | 4/1980 | Zeff et al. | |
| 4,236,482 A | 12/1980 | Gingerich et al. | |
| 4,256,094 A | 3/1981 | Kapp | |
| 4,277,706 A | 7/1981 | Issacson | |
| 4,304,225 A | 12/1981 | Freeman | |
| 4,454,891 A | 6/1984 | Dreibelbis et al. | |
| 4,457,673 A | 7/1984 | Conley et al. | |
| 4,459,977 A | 7/1984 | Pizon et al. | |
| 4,515,587 A | 5/1985 | Schiff | |
| 4,583,523 A | 4/1986 | Kleinke et al. | |
| 4,594,731 A | 6/1986 | Lewkowicz | |
| 4,630,597 A | 12/1986 | Kantrowitz et al. | |
| 4,676,482 A | 6/1987 | Reece et al. | |
| 4,697,574 A | 10/1987 | Karcher et al. | |
| 4,763,646 A | 8/1988 | Lekholm | |
| 4,771,765 A | 9/1988 | Choy et al. | |
| 4,809,676 A | 3/1989 | Freeman | |
| 4,813,952 A | 3/1989 | Khalafalla | |
| 4,822,357 A | 4/1989 | Forster et al. | |
| 4,881,939 A | 11/1989 | Newman | |
| 4,886,490 A * | 12/1989 | Shiber | 604/22 |
| 4,957,477 A | 9/1990 | Lundback | |
| 4,979,936 A | 12/1990 | Stephenson et al. | |
| 5,089,017 A | 2/1992 | Young et al. | |
| 5,169,378 A | 12/1992 | Figuera | |
| 5,197,980 A | 3/1993 | Gorahkov et al. | |
| 5,205,810 A | 4/1993 | Guiraudon et al. | |
| 5,222,980 A | 6/1993 | Gealow | |
| 5,267,940 A | 12/1993 | Moulder | |
| 5,273,518 A | 12/1993 | Lee | |
| 5,290,249 A | 3/1994 | Foster et al. | |
| 5,300,111 A | 4/1994 | Panton et al. | |
| 5,337,752 A | 8/1994 | Reeves | |
| 5,344,385 A | 9/1994 | Buck et al. | |
| 5,360,445 A | 11/1994 | Goldowsky | |
| 5,372,573 A | 12/1994 | Habib | |
| 5,429,584 A | 7/1995 | Chiu | |
| 5,447,523 A | 9/1995 | Schaldach | |
| 5,453,076 A | 9/1995 | Kiyota et al. | |
| 5,511,551 A | 4/1996 | Sano et al. | |
| 5,554,177 A | 9/1996 | Kieval et al. | |
| 5,569,156 A | 10/1996 | Mussivand | |
| 5,593,414 A | 1/1997 | Shipp et al. | |
| 5,607,378 A | 3/1997 | Winston | |
| 5,647,380 A | 7/1997 | Campbell et al. | |
| 5,722,930 A | 3/1998 | Larson, Jr. et al. | |
| 5,792,195 A | 8/1998 | Carlson et al. | |
| 5,814,012 A | 9/1998 | Fleenor et al. | |
| 5,820,542 A | 10/1998 | Dobak, III et al. | |
| 5,827,171 A | 10/1998 | Dobak, III et al. | |
| 5,843,170 A | 12/1998 | Ahn | |
| 5,975,140 A | 11/1999 | Lin | |
| 5,980,488 A | 11/1999 | Thorne | |
| 6,030,336 A | 2/2000 | Franchi | |
| 6,045,496 A | 4/2000 | Pacella et al. | |
| 6,066,085 A | 5/2000 | Heilman et al. | |
| 6,132,363 A | 10/2000 | Freed et al. | |
| 6,132,636 A | 10/2000 | Singh et al. | |
| 6,210,318 B1 | 4/2001 | Lederman | |
| 6,210,319 B1 | 4/2001 | Williams et al. | |
| 6,226,843 B1 | 5/2001 | Crainich | |
| 6,251,061 B1 | 6/2001 | Hastings et al. | |
| 6,406,422 B1 | 6/2002 | Landesberg | |
| 6,432,039 B1 | 8/2002 | Wardle | |
| 6,471,633 B1 | 10/2002 | Freed | |
| 6,553,263 B1 | 4/2003 | Meadows et al. | |
| 6,572,534 B1 | 6/2003 | Milbocker et al. | |
| 6,585,635 B1 | 7/2003 | Aldrich | |
| 6,616,596 B1 | 9/2003 | Milbocker | |
| 6,626,821 B1 | 9/2003 | Kung et al. | |
| 6,643,548 B1 | 11/2003 | Mai et al. | |
| 6,808,483 B1 | 10/2004 | Ortiz et al. | |
| 6,808,484 B1 | 10/2004 | Peters et al. | |
| 6,984,201 B2 | 1/2006 | Khaghani et al. | |
| 7,169,109 B2 | 1/2007 | Jansen et al. | |
| 7,306,558 B2 | 12/2007 | Peters et al. | |
| 7,347,811 B2 | 3/2008 | Peters et al. | |
| 7,357,771 B2 | 4/2008 | Peters et al. | |
| 7,513,864 B2 | 4/2009 | Kantrowitz et al. | |
| 7,740,575 B2 | 6/2010 | Peters et al. | |
| 7,766,049 B2 | 8/2010 | Miller et al. | |
| 2001/0016676 A1 | 8/2001 | Williams et al. | |
| 2003/0105497 A1 | 6/2003 | Zhu et al. | |
| 2004/0010180 A1 | 1/2004 | Scorvo | |
| 2004/0073080 A1 | 4/2004 | Peters et al. | |
| 2004/0097783 A1 | 5/2004 | Peters et al. | |
| 2004/0097784 A1 | 5/2004 | Peters et al. | |
| 2004/0147803 A1 | 7/2004 | Hegde et al. | |
| 2004/0152945 A1 | 8/2004 | Kantrowitz et al. | |
| 2006/0052866 A1 | 3/2006 | Gilles et al. | |
| 2007/0021830 A1 | 1/2007 | Peters | |
| 2007/0093684 A1 | 4/2007 | Peters et al. | |
| 2007/0129796 A1 | 6/2007 | Miller | |
| 2007/0135677 A1 | 6/2007 | Miller et al. | |
| 2007/0167898 A1 | 7/2007 | Peters et al. | |
| 2008/0027270 A1 | 1/2008 | Peters et al. | |
| 2008/0139873 A1 | 6/2008 | Peters et al. | |
| 2008/0167515 A1 | 7/2008 | Peters et al. | |
| 2008/0194905 A1 | 8/2008 | Walsh | |
| 2011/0196467 A1 | 8/2011 | Miller et al. | |
| 2011/0270331 A1 | 11/2011 | Peters et al. | |

FOREIGN PATENT DOCUMENTS

| | | |
|---|---|---|
| DE | 1541311 | 9/1969 |
| EP | 0080348 B2 | 5/1988 |
| EP | 0363203 | 4/1990 |
| EP | 0364799 | 4/1990 |
| EP | 0216042 | 3/1991 |
| EP | 0601804 | 6/1994 |
| EP | 1129736 | 9/2001 |
| FR | 2458288 | 1/1981 |
| FR | 2645739 | 10/1990 |
| FR | 2767874 | 3/1999 |
| GB | 2422114 | 4/2008 |
| JP | H6-510461 | 11/1994 |
| JP | 9-502376 | 3/1997 |
| JP | 9-503933 | 4/1997 |
| JP | 10-328297 | 12/1998 |
| JP | H11-285529 | 10/1999 |
| JP | 2000-000299 | 1/2000 |
| JP | 2000-510006 | 8/2000 |
| JP | 2001-276213 | 10/2001 |
| JP | 2003-135497 | 5/2003 |
| WO | WO9015630 A1 | 12/1990 |
| WO | WO 92/08500 | 5/1992 |
| WO | WO 93/08874 | 5/1993 |
| WO | WO 95/05122 | 2/1995 |
| WO | WO 95/28127 | 10/1995 |
| WO | WO 97/40755 | 11/1997 |
| WO | WO 98/05289 | 2/1998 |
| WO | WO 98/14239 | 4/1998 |
| WO | WO 98/51367 | 11/1998 |
| WO | WO 99/02213 | 1/1999 |
| WO | WO 99/04833 | 2/1999 |
| WO | WO 99/45981 | 9/1999 |
| WO | WO 00/12168 | 3/2000 |
| WO | WO 00/76288 | 12/2000 |
| WO | WO 01/13974 | 3/2001 |
| WO | WO 01/83001 | 11/2001 |
| WO | WO 02/24254 | 3/2002 |
| WO | WO 02/24255 | 3/2002 |
| WO | WO 02/076305 | 10/2002 |
| WO | WO 03/011365 | 2/2003 |
| WO | WO 03/028787 | 4/2003 |
| WO | WO 2004/045677 | 6/2004 |
| WO | WO2005/041783 A1 | 5/2005 |
| WO | WO 2005/042063 | 5/2005 |
| WO | WO 2005/044338 | 5/2005 |
| WO | WO2005/110512 A1 | 11/2005 |
| WO | WO 2008/053469 | 5/2008 |
| WO | WO 2008/071223 | 6/2008 |

OTHER PUBLICATIONS

J.L. Stewart, "Aortic Cuff a Cardiac Assistance Device", Polytechnic Institute of Brooklyn, 1968, pp. 9-108.
Hiroshi Odaguchi et al., "Experimental Study of Extraaortic Balloon Counterpulsation as a Bridge to Other Mechanical Assists" ASAIO Journal, pp. 190-194, vol. 42, No. 3, Lippincott Williams & Wilkins/ASAIO, Hagerstown, MD, May 1, 1996. cited by other.
"Use of Heart Valve Sounds as Input to Cardiac Assist Devices", Research Disclosures, Mar. 1995.
Luisada et al., On the Function of the Aortic Valve and the Mechanism of the First and Second Sounds, Japanese Heart Journal, vol. 18(1), Jan. 1977, pp. 81-91.
International Search Report issued in PCT/AU00/00654, mailed Aug. 18, 2000, 5 pages.
International Search Report issued in PCT/AU2002/000974, mailed Oct. 11, 2002, 5 pages.
International Preliminary Examination Report issued in PCT/AU2002/000974, completed Aug. 11, 2003, 8 pages.
International Search Report issued in PCT/AU2001/01187, mailed Nov. 5, 2001, 3 pages.
International Preliminary Examination Report issued in PCT/AU2001/01187, completed May 2, 2002, 4 pages.
International Search Report and Written Opinion issued in PCT/AU2007/001188, mailed Oct. 4, 2007, 12 pages.
International Preliminary Report on patentability, Chapter II, issued in PCT/AU2007/001188, completed Mar. 11, 2008, 8 pages.
International Search Report issued in PCT/AU2003/001450, mailed Feb. 2, 2004, 2 pages.
International Preliminary Examination Report issued in PCT/AU2003/001450, completed Mar. 2, 2005, 4 pages.
International Search Report issued in PCT/AU2003/001458, mailed Feb. 5, 2004, 5 pages.
International Prelminary Examination Report issued in PCT/AU2003/001458, completed Mar. 7, 2005, 7 pages.
International Search Report and Written Opinion issued in PCT/AU2004/001483, mailed Nov. 26, 2004, 5 pages.
International Search Report and Written Opinion issued in PCT/AU2004/001484, mailed Nov. 29, 2004, 5 pages.
International Search Report and Written Opinion issued in PCT/AU2004/01485, mailed Feb. 7, 2005, 6 pages.
International Search Report and Written Opinion issued in PCT/AU2004/001486, mailed Jan. 6, 2005, 7 pages.
International Search Report and Written Opinion issued in PCT/AU2004/01487, mailed Jan. 27, 2005, 12 pages.
International Search Report and Written Opinion issued in PCT/AU2004/01488, mailed Dec. 15, 2004, 6 pages.
Supplemental European Search Report issued in EP Application 00934813, mailed 0/19/2006, 2 pages.
Supplemental European Search Report issued in EP 01971489, completed Nov. 22, 2006, 4 pages.
Supplemental European Search Report issued in EP App No. 02748447, Feb. 6, 2007, 6 pages.
Supplemental European Search Report issued in EP App. No. 04789624, mailed Mar. 6, 2008, 7 pages.
Supplemental European Search Report issued in EP 04789625, mailed Nov. 18, 2009, 6 pages.
Office Action issued in JP Application No. 2004-552261, dated Mar. 2, 2010.

* cited by examiner

WRAP FOR A HEART ASSIST DEVICE

TECHNICAL FIELD

The present invention relates to an improved wrap generally for a heart assist device and, more particularly, for a counterpulsation heart assist device.

The invention has been developed as an improvement over the type of wrap disclosed in the Applicant's International Patent Application No. PCT/AU2004/001484 (WO 2005/041783), hereafter "the wrap PCT application", and for use with the type of balloon actuators disclosed in the Applicant's International PCT Patent Application No. PCT/AU2004/001487 (WO 2005/044338), hereafter "the actuator PCT application". However, it will be appreciated that the improved wrap is also suitable for use with other heart assist devices that use inflatable actuators.

BACKGROUND OF THE INVENTION

The wrap disclosed in the wrap PCT application is formed from an elongate piece of woven polyester (or similar non-absorbable bio-stable and bio-compatible material). When laid on a planar surface, the wrap is substantially flat or planar. The wrap includes an opening for a fluid tube to be connected to the inflatable balloon or chamber of a heart assist device. The wrap also includes a thinned portion with a pair of curved longitudinal slits which assist in preventing the wrap from kinking, folding or pleating in the thinned portion when wrapped around a curved portion of an aorta.

Parts of the side of the wrap disclosed in the wrap PCT application have a series of spaced apart slits, which are substantially normal to the longitudinal axis of the wrap. The purpose of the slits is to make those parts of the wrap sides more elastic or stretchable than the intermediate central portion of the wrap. As a result, when the wrap disclosed in the wrap PCT application is placed around a curved arterial vessel, such as an ascending aorta, and tightened to a snug fit, less tension is placed in the sides or edges of the wrap than in the centre. This avoids the depression/kinking, and associated high strain levels, associated with earlier wraps without such slits.

OBJECT OF THE INVENTION

It is an object of the present invention to provide an improved wrap compared to that disclosed in the wrap PCT application, and in a preferred form, a wrap that provides a better anatomical fit around the actuator of a heart assist device and the aorta or other arterial vessel to which it is applied.

SUMMARY OF THE INVENTION

Accordingly, in a first aspect, the present invention provides, in a heart assist device in which an inflatable balloon or chamber is held against an outside surface of a curved arterial vessel by a wrap formed from a flexible sheet-like material, the wrap having a first end portion, a second end portion and an intermediate portion connecting together the first and second end portions, the intermediate portion comprising at least three separate elongate sections arranged in side by side array each connected at each end to a respective one of the end portions of the wrap, the improvement in that the laterally outer ones of the elongate sections are longer than the central one of them.

As a result, if a wrap according to the first aspect of the invention defined above was laid on a planar surface, a central one of the elongate sections would lie substantially in that plane and the laterally outer ones of the elongate sections would, intermediate their ends, project above that plane.

In a second aspect, the present invention provides, in a heart assist device in which an inflatable balloon or chamber is held against an outside surface of a curved arterial vessel by a wrap formed from a flexible sheet-like material, the wrap having an inside surface and an outside surface and having a first end portion, a second end portion and an intermediate portion connecting together the first and second end portions, the intermediate portion comprising at least three separate elongate sections arranged in side by side array each connected at each end to a respective one of the end portions of the wrap, the improvement in that the laterally outer ones of the elongate sections are longer than the central one of them.

Preferably, the laterally outer edges of the elongate sections are longer than the laterally inner edges of the respective elongate sections. If such a wrap were laid on a planar surface the outer edges of each outer elongate section would project above that surface more than the corresponding inner edge.

It is also preferable that the three elongate sections each have a longitudinal axis and the axes of the two laterally outer elongate sections diverge from one another and from the central elongate section along their length from the intermediate portion to each end portion.

In a third aspect, the present invention provides, in a heart assist device in which an inflatable balloon or chamber is held against an outside surface of a curved arterial vessel by a wrap formed from a flexible sheet-like material, the improvement whereby if the wrap were laid on a planar surface it would include a dome-like portion extending away from that surface.

The dome-like shape is preferably at least partially formed by heat setting of the sheet-like material adjacent an end of the wrap, most preferably by heat setting between corresponding convexly and concavely shaped mould surfaces. The dome-like shape is preferably at least partially formed by removing substantially triangular sections of the to material and then joining edges of the material the adjacent removed portions, most preferably joining by gluing and/or suturing.

In a fourth aspect, the present invention provides an improved wrap for a heart assist device, the heart assist device includes an inflatable balloon or chamber adapted for placement against a curved arterial vessel, the wrap being of flexible, substantially non-elastic construction and adapted to, when encircling the balloon/chamber and the arterial vessel to locate the balloon/chamber against the artery at a tension lower than would substantially deform the vessel, adopt a shape substantially conforming to the exterior surfaces of the inflated balloon/chamber and arterial vessel in contact with the wrap.

The arterial vessel is preferably curved in two planes and the wrap substantially conforms to the two plane curvature.

The wrap is preferably a fabric weave and has some elastic properties due to it being cut on the bias, most preferably at 45 degrees to the warp/weft of the fabric weave.

The wrap preferably adopts said shape substantially conforming to the exterior surface of the balloon/chamber and artery substantially without wrinkles or folds.

The wrap preferably includes one or more cutouts and/or overlapping portions configured to allow it to substantially conform, in use, to the exterior surface of the balloon/chamber and arterial vessel. The wrap is preferably shaped to substantially conform, in use, to the exterior surface of the balloon/chamber and a curved arterial vessel. The wrap is preferably shaped to substantially conform, in use, to the exterior surface of the balloon/chamber and the ascending aorta, most preferably with the balloon/chamber positioned on the outer, convex side of the ascending aorta.

The wrap is preferably generally elongate with two sides and two ends, and includes: a relatively wide suture tab at one of the ends; and a relatively narrow pull tab on the other of its ends. The wrap preferably includes: a first relatively wide portion adjacent the suture tab, adapted to conform to the surface of the balloon/chamber remote the arterial vessel; a second relatively wide portion adjacent the pull tab, adapted to conform to the surface of the arterial vessel substantially adjacent the balloon/chamber; and a relatively narrow portion between the first and second relatively wide portions, adapted to conform to the surface of the arterial vessel not in contact with the balloon/chamber.

The first relatively wide portion and the relatively narrow portion preferably include spaced apart slits along their outer sides or edges.

The wrap preferably includes a buckle initially positioned on the suture tab, the buckle being adapted to receive therethrough the relatively narrow pull tab during positioning of the wrap and balloon/chamber around the arterial vessel.

The pull tab is preferably formed from two layers of the wrap material, most preferably from two layers of a single piece of wrap material that are folded and bonded to one another.

The heart assist device preferably includes a fluid inlet/outlet port and the wrap preferably includes a port opening. The port opening is preferably surrounded by a substantially domed surface, most preferably a truncated, ovular domed surface, that tapers outwardly away from the port opening. The port opening is preferably in the first relatively wide section of the wrap. Preferably, the domed surface has one edge longer than the other and a central axis that is concave towards the suture tab.

The wrap preferably includes two substantially longitudinal, curved cutouts in the relatively narrow portion between the first and second relatively wide portions.

In a fifth aspect, the present invention provides a method of forming an improved wrap for a heart assist device, the heart assist device includes an inflatable balloon or chamber adapted for placement against a curved arterial vessel, the method including forming a flexible, substantially non-elastic material into a shape that, when the wrap is positioned encircling the balloon/chamber and the arterial vessel to locate the balloon/chamber against the arterial vessel at a tension lower than would substantially deform the vessel, substantially conforms to the exterior surfaces of the inflated balloon/chamber and the arterial vessel in contact with the wrap.

The method preferably includes forming one or more cutouts and/or overlapping portions in the wrap, such cutouts/portions being configured to allow the wrap to substantially conform to the exterior surface of the balloon/chamber and artery, most preferably without wrinkles or folds.

The heart assist device preferably includes a fluid inlet/outlet port and the method preferably includes forming a port opening in the wrap that is surrounded by a substantially domed surface, most preferably a truncated, ovular domed surface, that tapers outwardly away from the port opening.

In a sixth aspect, the present invention provides an improved wrap for a heart assist device, the heart assist device includes an inflatable balloon or chamber adapted for placement against a curved arterial vessel, the wrap being of flexible, substantially non-elastic construction which, when developed along its longitudinal direction, includes a substantially domed surface.

The domed surface is preferably in the form of a truncated, ovular domed surface that tapers inwardly away from the remainder of the wrap. The domed surface preferably includes a fluid inlet/outlet port opening therein, most preferably at the apex of the dome. The domed surface is preferably formed in a relatively wide portion of the wrap.

The wrap preferably also includes a suture tab adjacent one side of the domed surface.

The wrap preferably also includes a relatively narrow portion with longitudinally extending, curved slits therein, on the other side of the domed surface. In the relatively narrow portion, the wrap material that is between the side of the wrap and the slits is preferably longer in the longitudinal direction than the wrap material between the two slits.

The wrap preferably includes a further relatively wide portion adjacent the side of the relatively narrow portion that is remote the domed surface. The wrap preferably also includes a pull tab adjacent the further relatively wide section, with the pull tab forming one end of the wrap and the suture tab forming the other end of the wrap.

In a particularly preferred embodiment of the invention the wrap is cut from a single piece of a flexible sheet-like material at a 45 degree bias. A blank is preferably cut from the sheet-like material including a first end portion, a second end portion and an intermediate portion comprising at least three separate elongate sections arranged in side by side array with at least the central one of those elongate sections connecting the first and second end portions and the laterally outer ones of the elongate sections being only connected to an end portion at one of their ends. In addition the blank preferably includes at least one extension piece that can be folded back over an end portion and connected the free end of at least one of the laterally outer elongate sections so that the length of that laterally outer elongate section is longer than the central one of the elongate sections.

BRIEF. DESCRIPTION OF THE DRAWINGS

A preferred embodiment of the invention will now be described, by way of an example only, with reference to the accompanying drawings in which.

DETAILED DESCRIPTION OF THE PREFERRED EMBODIMENT

Figure 1:
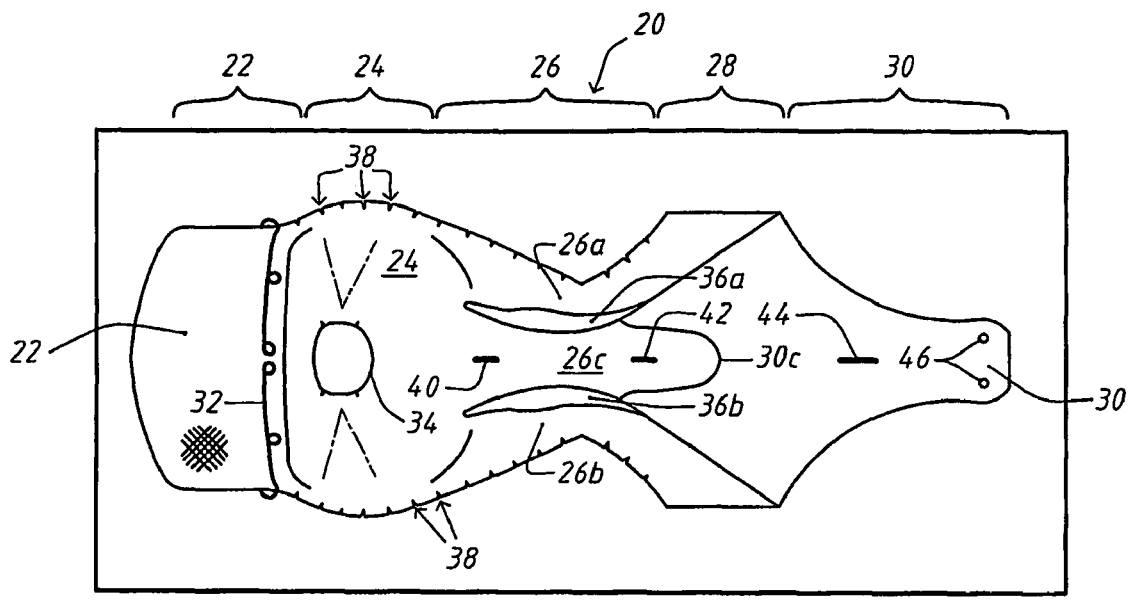
FIG. 1 is a developed plan view of an embodiment of an improved wrap.

Turning firstly to FIG. 1, there is shown an embodiment of an improved wrap 20 for use with, for example, a heart assist device of the type shown in the actuator PCT application. The wrap 20 is formed from an elongate piece of woven polyester, or similar non-absorbable, bio-stable and bio-compatible material. In contrast to the wrap disclosed in the wrap PCT application, the wrap 20, when developed or extended along its longitudinal direction (as shown), is not substantially planar but instead includes three dimensional portions which will be described in more detail below.

The wrap 20 is generally comprised of five portions namely: a relatively wide suture tab 22; a relatively wide domed portion 24; a relatively narrow slotted portion 26; a relatively wide planar section 28; and a pull tab 30. The planar section 28 also acts as a suture tab as it mates with the tab 22 after encircling the vessel, which will be described in more detail below.

The suture tab 22 includes a buckle 32 at its proximal end. The buckle 32 is of the type shown in the Applicant's International PCT Patent Application No. PCT/AU2004/001488 (WO 2005/041781), hereafter "the buckle PCT application". The buckle 32 receives the pull tab 30 therethrough during the implantation of a heart assist device, as is described in the buckle PCT application. The relevant contents of the buckle PCT application are incorporated herein by cross reference.

When the wrap 20 is laid on a planar surface, the domed surface 24 curves outwardly away from that plane. The domed surface 24 has a generally ovular cross-sectional shape and an inlet/outlet port opening 34 at its apex or geometric centre. The domed surface 24 tapers outwardly away from the opening 34 to the remainder of the wrap 20. The fluid inlet/outlet tube of an actuator is positioned through the opening 34 prior to implantation of a heart assist device. The domed shape of the surface 24 substantially corresponds to the exterior shape of an inflated balloon/chamber type actuator, when implanted on an arterial vessel. The domed surface 24 also has a curvature to fit the secondary radius of the aorta. The steps included in forming of the domed surface 24 will be described in more detail below.

The portion 26 includes a pair of longitudinally extending curved openings or slits 36a and 36b, similar to the slits 32 shown in the wrap PCT application. The slits 36a and 36b divide the portion 26 into three parts or strips, namely: two outer strips 26a and 26b, which are between the side of the wrap 20 and each of the slits 36a and 36b; and also a central strip 26c which is between the slits 36a and 36b. The laterally outer strips 26a and 26b are longer than the central strip 26c. When the wrap 20 is laid on a planar surface, the central strip 26c lies substantially in that plane, whereas the laterally outer strips 26a and 26b, being longer, project out of that plane. If the material of the wrap is is relatively stiff the outer strips 26a and 26b will curve upwardly out of the plane. If the material is softer and more flexible then the projection out of the plane will be more in the nature of crumpling of the material above the plane. Further, the laterally outer edges of the outer strips 26a and 26b curve, intermediate their ends, more upwardly out of that plane than the laterally inner edges of the outer strips 26a and 26b. It is also to be noted that the longitudinal axes of the strips 26a and 26b diverge from one another, and from the central strip 26c, as they extend from the central portion 26 (relatively narrow) to the planar portion 28 and domed portion 24.

The strips 26a and 26b are longer than the strips 26c in the longitudinal direction of the wrap 20. As a result, when the wrap 20 encircles a curved arterial vessel (e.g. an ascending aorta) with the slits 36a, 36b positioned against the inner concave surface of the vessel, at a tension lower than would substantially deform the vessel, the strips 26a, 26b and 26c gather together in a manner substantially conforming to the adjacent surface of the vessel without kinking or folding. Moreover, the strips 26a, 26b and 26c conform to the adjacent surfaces of the vessel more closely than the equivalent components of the wrap disclosed in the wrap PCT application, which all had a corresponding length in the longitudinal direction of the wrap. The different lengths of the strips 26a, 26b and 26c also allows for the maintenance of the same elastic properties at each location normal to the longitudinal axis of the vessel. The manufacture of the outer strips 26a and 26b shall be described in more detail below.

The pull tab 30 is formed from two layers of the wrap material, as opposed to the one layer that forms the remainder of the wrap 20, in order to increase its rigidity. This makes the pull tab 30 easier to handle and position by a surgeon during implantation of a heart assist device.

The external edges or sides of the portions 24 and 26 include a series of spaced apart slits 38. The slits 38 result in those parts of the sides of the wrap 20 being more elastic or stretchable than the intermediate central portion of the wrap 20. As a result, when the wrap is placed around the aorta and tightened to a snug fit, less tension is placed in the sides or edges of the wrap 20 than in the centre. This avoids the depression/kinking, and associated high strain levels, associated with earlier wraps, as is discussed in the wrap PCT application.

The wrap 20 also includes two small slots 40 and 42 and a large slot 44. The slots 40, 42 and 44 are used as location points during the manufacture of the wrap, as will be discussed in more detail below. Slot 44 is used for allis clamps or forceps during implant to allow the wrap to be tensioned using standard length surgical instruments. The slots 40 and 42 also provide areas to enable revascularization or improved blood supply under the wrap 20 when implanted.

The wrap 20 also includes one, two or three size identification markings, in the form of one or more dots 46 adjacent the pull tab 30. One dot indicates a 'small' size wrap. Two dots indicate a 'medium' size wrap. Three dots indicate a 'large' size wrap.

The manufacture of the wrap 20 shall now be described with reference to FIGS. 2 to 15. All steps in the manufacture of the wrap 20 are performed in a controlled environment room (CER) with all of the operator's material and tools being cleaned to applicable standards.

Figure 2:
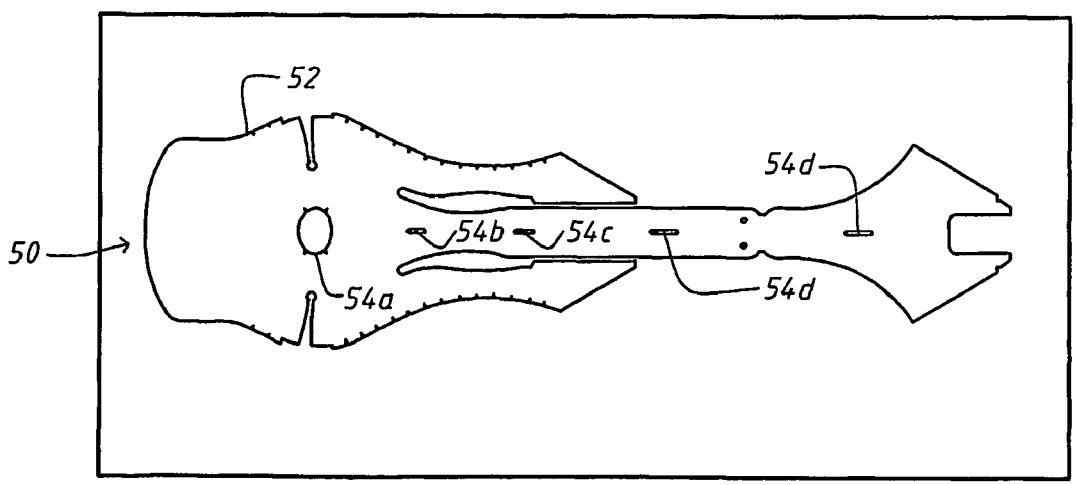
FIG. 2 is a plan view of a cutting template for the wrap shown in FIG. 1 atop a piece of wrap material.

FIG. 2 shows a stainless steel cutting template 50 adjacent a piece of wrap material 52. The first stage in the production of the wrap 20 is to iron the wrap material 52. The ironing is conducted at a linen/dry heat setting. The material 52 in the template's five central openings 54a, 54b 54c, 54d (2 of) is then cut and removed in order to form the openings 34, 40, 42 and 44 respectively. The material 52 exterior to the wrap template 50 is then cut and removed. The material 52 is cut on its bias, at 45 degrees to the warp/weft of the fabric weave. This allows the warp and weft fibres to change angle relative to one another and therefore increase and decrease longitudinally when force is applied or removed, which improves the ability of the wrap 20 to conform to the aorta. The C shaped cut out 30c between the tail ends 30b ensures only a single layer of material is in the suturing region. This single layer also reduces the stiffness of the wrap when conforming to the aorta.

Figure 3:
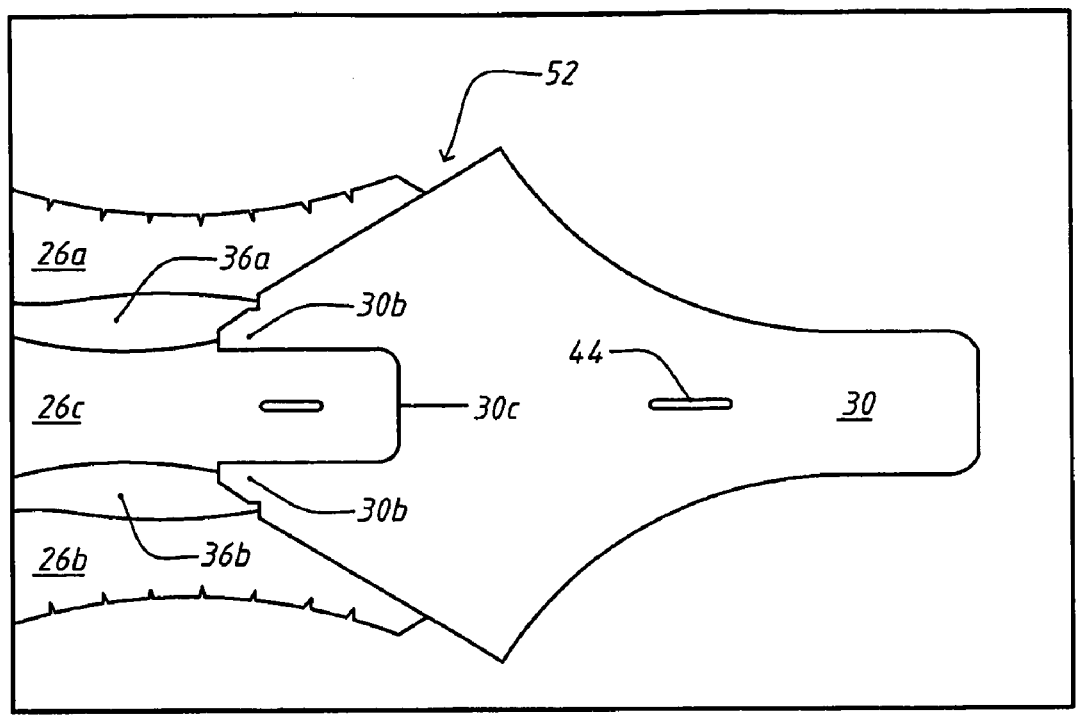
FIG. 3 is an enlarged detail view of the pull tab end of the wrap shown in FIG. 1 prior to adhesive bonding.

With reference to FIG. 3, the right hand end of the wrap material 52 is folded over itself to align the two openings 54d that form the large slot 44 in order to form the pull tab 30. The fold at the distal end of the pull tab 30 is then ironed with tail ends 30b aligned with the ends of the slits 36 to create a smooth transition between these parts. This folding also provides a portion for attaching the adjacent ends of the strips 26a and 26b, as will be described in more detail below, whilst also conveniently permitting the wrap 20 to be produced from a single piece of material.

Figure 4:
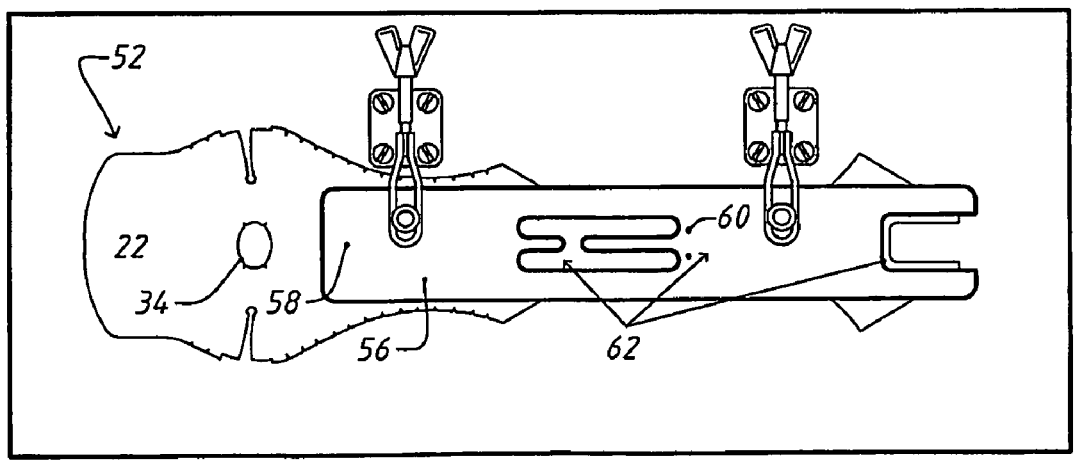
FIG. 4 is a plan view of an adhesive template atop the cut piece of fabric used to form the wrap shown in FIG. 1.
Figure 5:
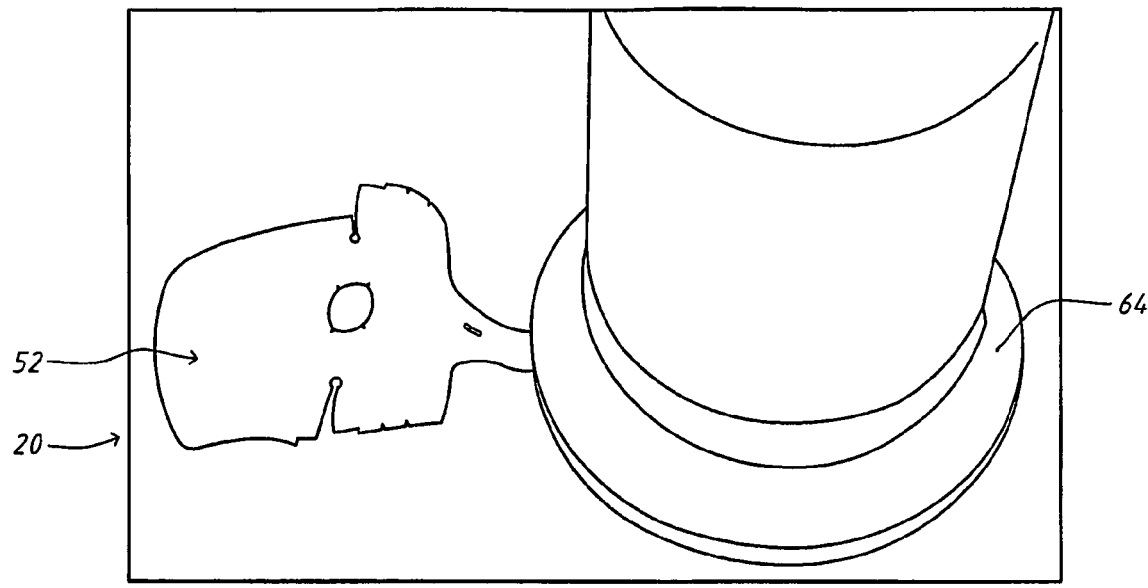
FIG. 5 is a perspective view of the wrap of FIG. 1 with one end undergoing gluing and clamping.

As shown in FIG. 4, the folded wrap material 52 is then positioned under an adhesive template 56. The template 56 includes alignment holes 58 and 60. The alignment hole 58 is aligned with the small slot 40. The alignment hole 60 is aligned with the size identification markings 46. The holes 58, 60 thus provide references to enable the wrap material to be accurately positioned in relation to the template 56 and ensure the correct size template is used. The exposed edge of the wrap material 52 is then traced with adhesive in the three locations indicated by arrows 62. The template 62 is then removed and the wrap material 52 is folded to the position shown in FIG. 3 and clamped under a load 64, as shown in FIG. 5, until the adhesive cures. The load 64 is then removed leaving the wrap material 52 shown in FIG. 6.

Figure 6:
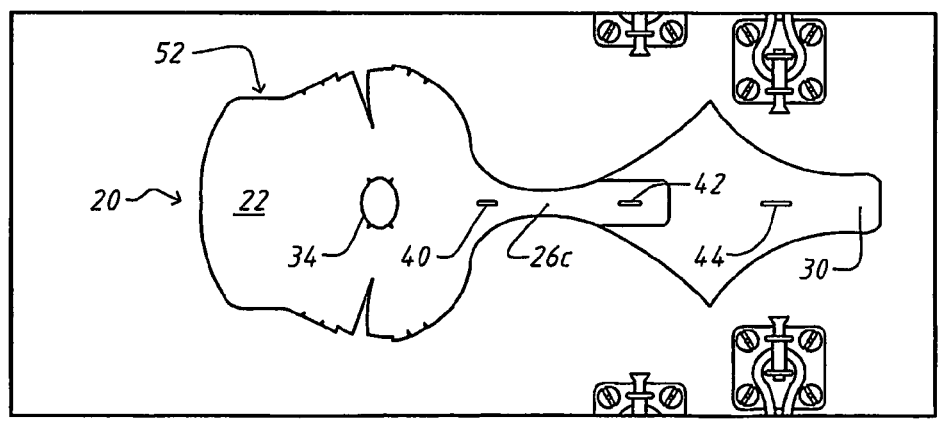
FIG. 6 is a plan view of the wrap shown in FIG. 1 upon removal from an adhesive clamp.
Figure 7:
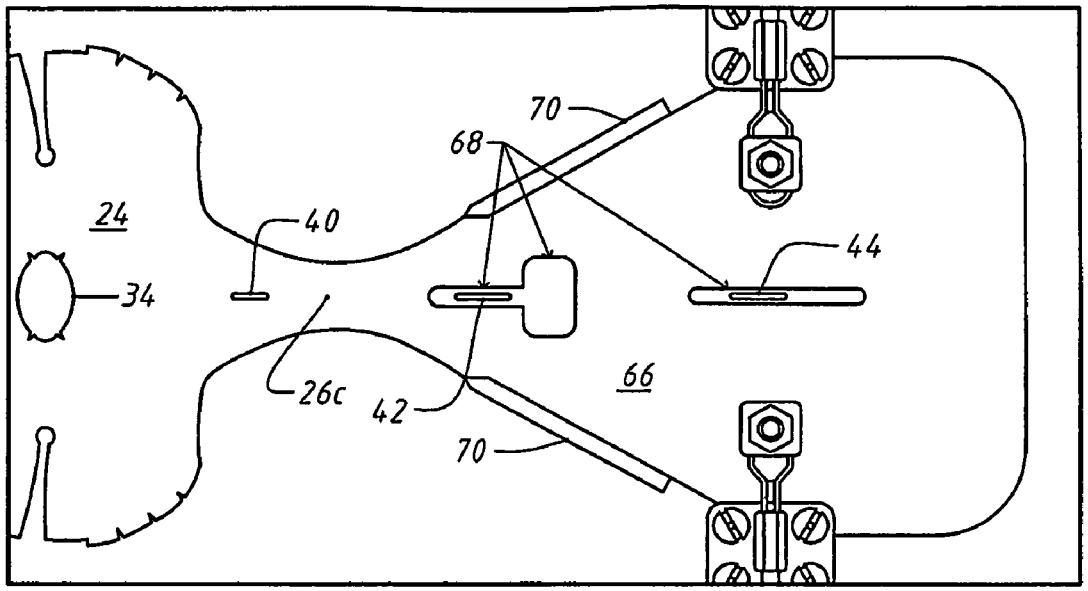
FIG. 7 is a partial detail view of the wrap shown in FIG. 1 beneath an adhesive template.
Figure 8:
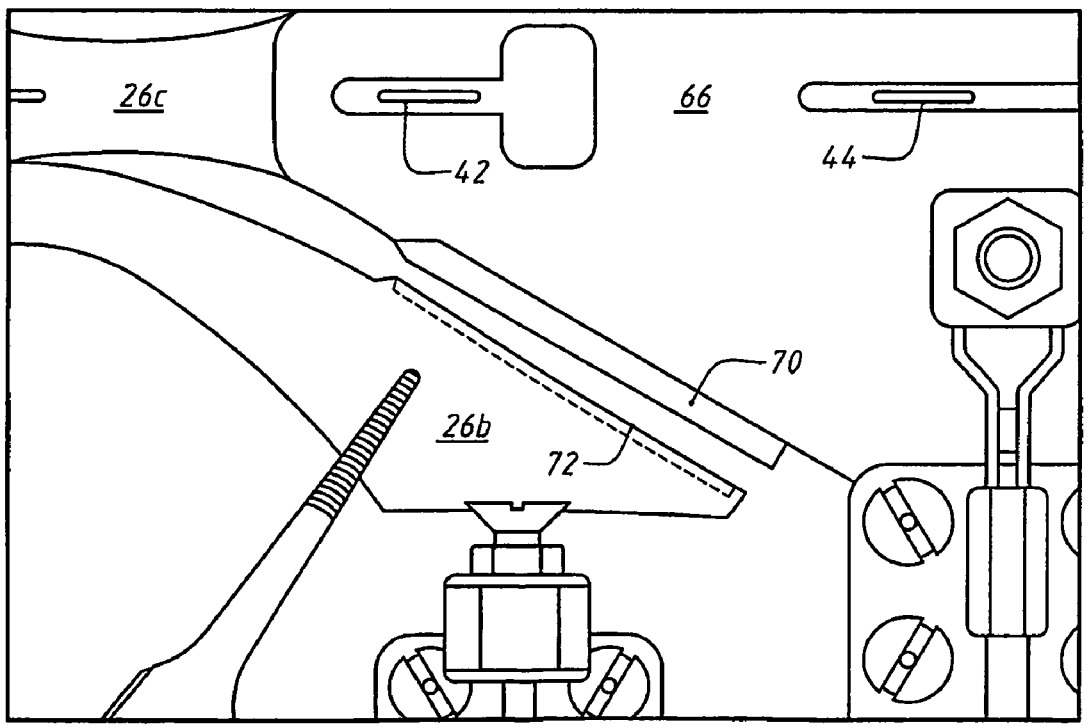
FIG. 8 is an enlarged detailed view of the wrap/template shown in FIG. 7 gluing operation.
Figure 9:
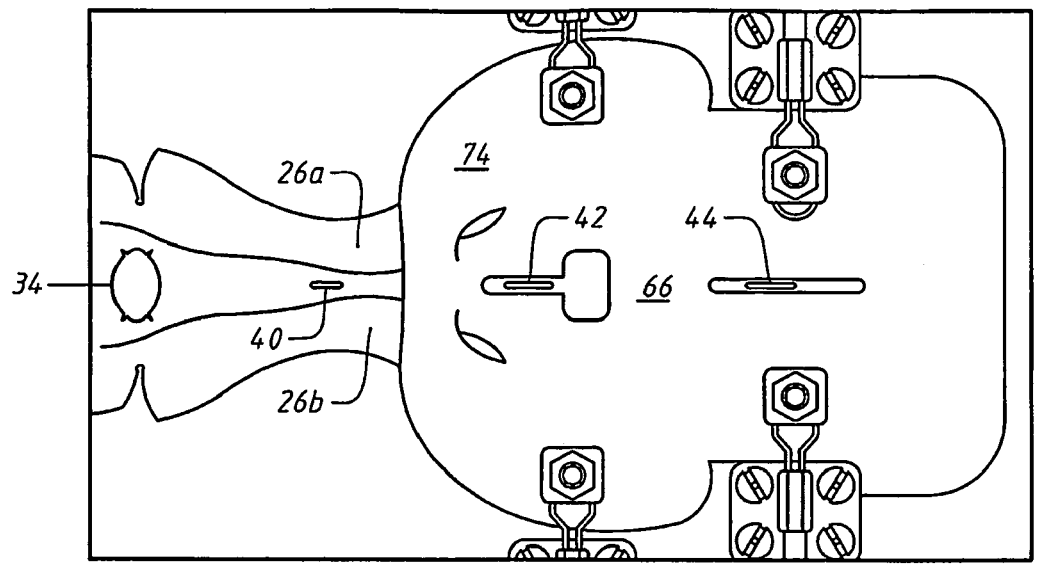
FIG. 9 is a plan view of the wrap/template shown in FIG. 8 subsequent to the gluing operation.
Figure 10:
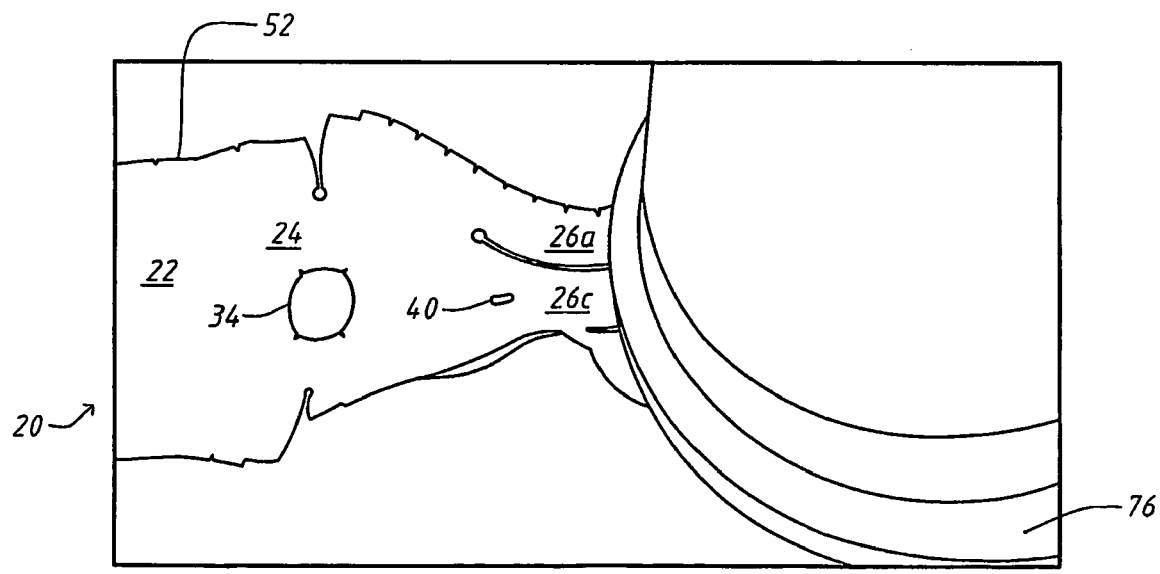
FIG. 10 shows the wrap of FIG. 9 being clamped after the gluing operation.

FIG. 7 shows the wrap material of FIG. 6 clamped beneath an adhesive template 66 (with the strips 26a and 26b folded out of the way towards the suture tab 22). The template 66 is aligned with the wrap material 52 at the three locations indicated by arrows 68. Adhesive is then applied along the exposed edges 70 of the pull tab 30. As shown in FIG. 8, the outer strips 26a and 26b then have their edges 72 positioned in contact with the adhesive 70. The edge 72 is attached to the wrap material closer to the pull tab end of the wrap 20 compared to from where it was cut and on a 30 deg angle from it's original cut edge. This longitudinal repositioning results in the outer strips 26a and 26b, intermediate their ends, curving away from the remainder of the wrap 20 when the wrap 20 is positioned on a flat surface. The edge 72 is also attached more outwardly than compared to from where it was cut. This lateral repositioning results in the laterally outer edges of the outer strips 26a and 26b, intermediate their ends, curving away more from the remainder of the wrap 20 than the laterally inner edges of the outer strips 26a and 26b. In addition, the laterally outer edge of strips 26a and 26b when positioned on edge 72 provide a straight section 28 with edges parallel to the central longitudinal axis of the wrap 20 providing suture region adjustable for within a defined range of vessel diameters As shown in FIG. 9, an additional clamping template 74 is then positioned over the overlapping surfaces 70 and 72 being glued together. As best shown in FIG. 10, a load 76 (similar to the load 64) is then applied to the clamped surfaces until the adhesive has cured.

Figure 11:
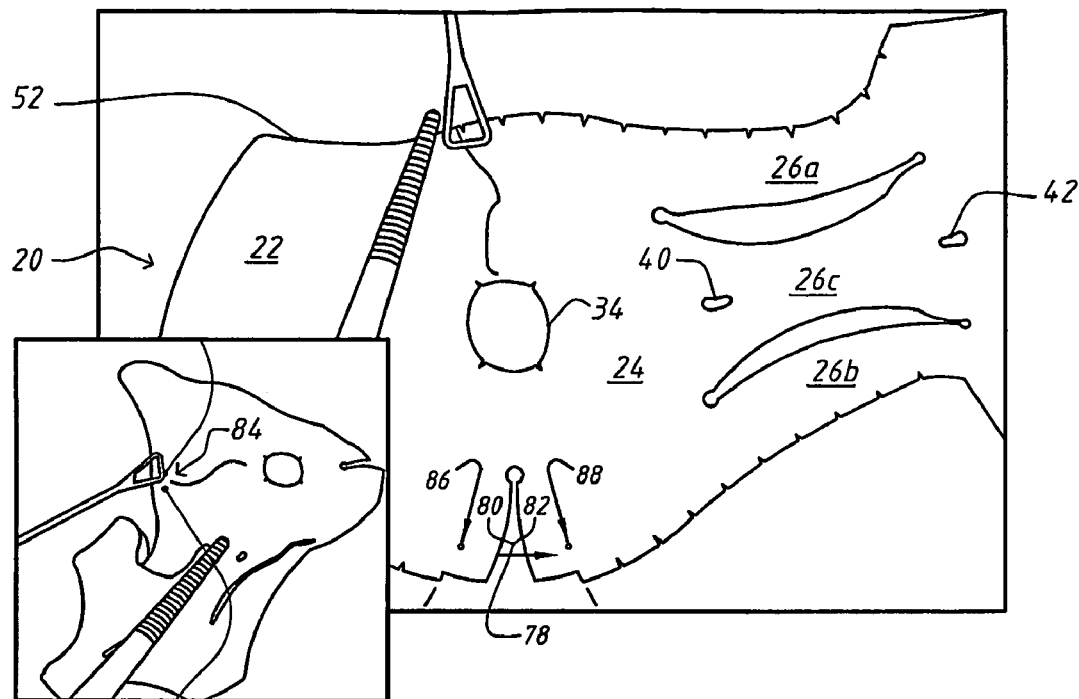
FIG. 11 shows two views of the wrap of FIG. 1 during suturing adjacent to fluid inlet/outlet port opening.

As shown in FIG. 11, the wrap material 52 has a substantially triangular section removed at 78 either side of the opening 34. The edges 80 and 82 either side of the removed section are then overlapped, to form a slot at the edge, and initially held in this position by a suture 84 passing through location 86 and 88. A similar procedure is performed on the opposite side of the wrap material 52. This forms the basis for producing the domed surface 24.

Figure 12:
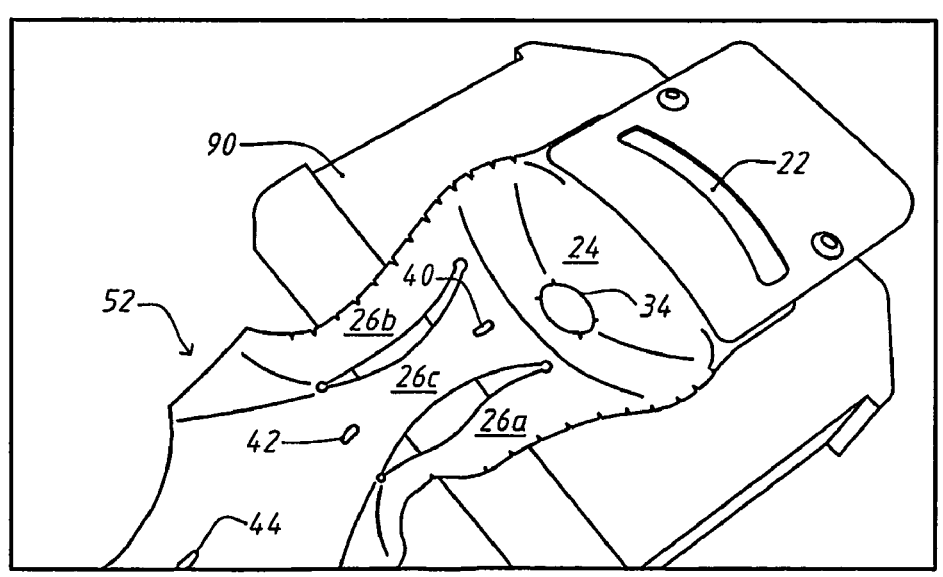
FIG. 12 shows the wrap of FIG. 11 positioned in a clamp prior to a heat setting operation.

As shown in FIG. 12, the sutured wrap material 52 is then positioned within a mould 90 with an outwardly concave or female recess with an arc on its main axis corresponding in shape an inflated actuator for a heart assist device. The wrap material 52 adjacent the domed surface 24 is then heat shaped by applying a male outwardly convex dome to apply heat consistently across the surface, adding folds in the correct location and heat shaping the remainder. The heat is provided by an iron applied to the mould parts whilst they are clamped together. The ironing is conducted at a linen/dry heat setting for approximately 20 to 30 seconds. The overlapped material and the deformation caused by the moulding and the iron's heat produces the smooth domed surface 24.

Figure 13:
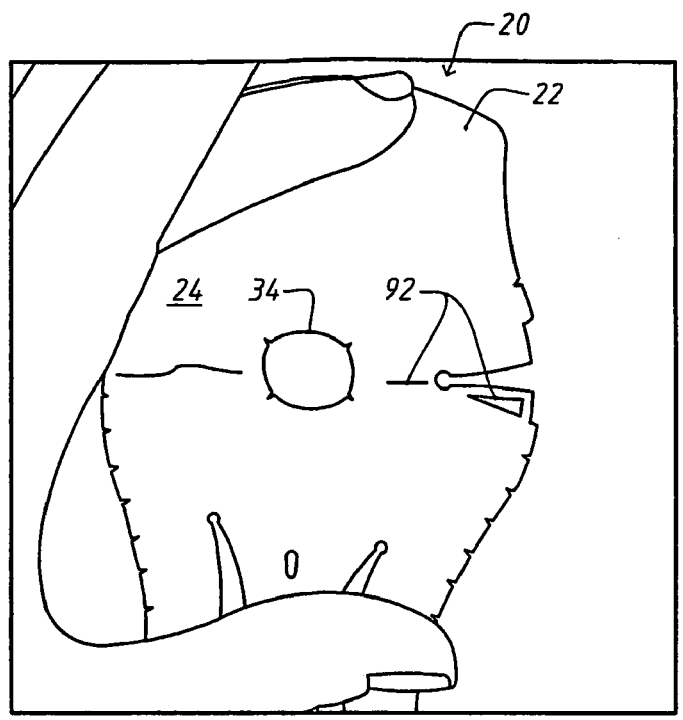
FIG. 13 shows the wrap of FIG. 12 with adhesion locations highlighted.
Figure 14:
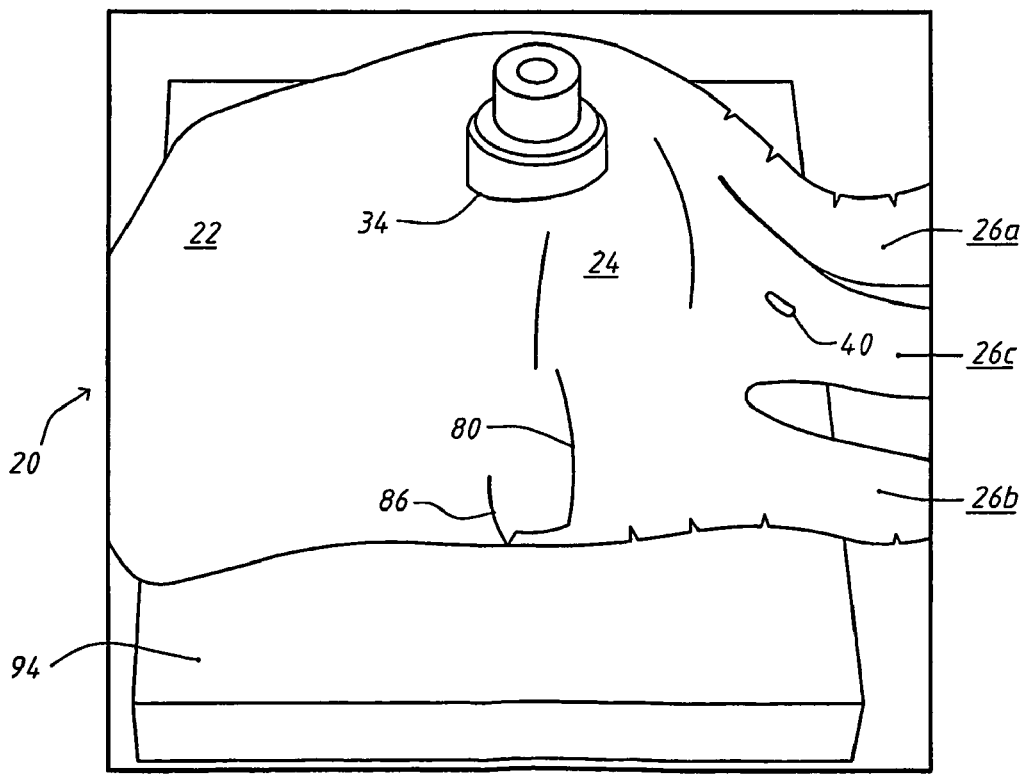
FIG. 14 shows the wrap of FIG. 13 after the gluing operation and adjacent the male part of an adhesive clamp.
Figure 15:
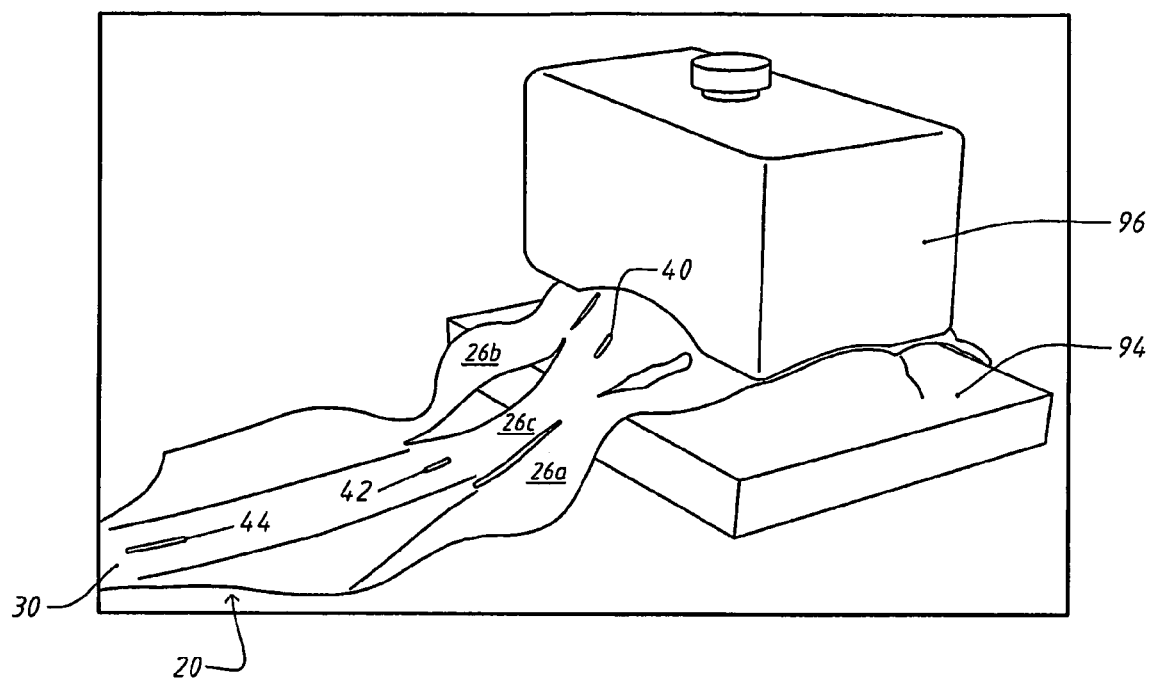
FIG. 15 shows the wrap of FIG. 14 during a clamping operation adjacent the fluid inlet/outlet port opening.

As shown in FIG. 13, the sutures 84 are then removed and the overlapped parts of the wrap material 52 are separated so that adhesive can be applied where indicated by arrows 92. As shown in FIG. 14, the previously overlapped parts of the wrap material 52 are then repositioned in contact with one another and placed over a male mould part 94. As shown in FIG. 15, a corresponding female mould part 96 is then used to clamp the overlapping surfaces until the adhesive cures.

The use of the wrap 20 in the implantation of a heart assist device is substantially identical to that descried in the buckle PCT application. The relevant contents of which are incorporated herein by cross reference.

The wrap 20 formed by the above process, will, when implanted encircling the balloon or chamber of a heart assist device and a curved arterial vessel (eg. the ascending aorta) at a tension lower than would substantially deform the vessel, will substantially conform to the adjacent exterior surfaces of the balloon, chamber and arterial vessel that are in contact with the wrap. More particularly, the wrap 20 will substantially conform to the exterior surface of the balloon, chamber and arterial vessel substantially without wrinkles or folds, whereby the application of force from actuation of the balloon/chamber will be effectively translated normal to the axis of the vessel at any location along the vessel.

Although the invention has been described with reference to a preferred embodiment, it will be appreciated that the invention is not limited to this particular embodiment and may be embodied in many other forms.

The invention claimed is:

1. In a heart assist device in which an inflatable balloon or chamber is held against an outside surface of a curved arterial vessel by a wrap formed from a flexible sheet-like material, the wrap having a first end portion, a second end portion and an intermediate portion connecting together the first and second end portions, the intermediate portion comprising at least three separate elongate sections arranged in side by side array each connected at each end to a respective one of the end portions of the wrap, the improvement in that the laterally outer ones of the elongate sections are longer than the central one of them.

2. The heart assist device as claimed in claim 1, wherein the three elongate sections each have a longitudinal axis and the axes of the two laterally outer elongate sections diverge from one another and from the central elongate section along their length from substantially a mid point of the intermediate portion to each of the end portions.

3. In a heart assist device in which an inflatable balloon or chamber is held against an outside surface of a curved arterial vessel by a wrap formed from a flexible sheet-like material, the wrap having an inside surface and an outside surface and having a first end portion, a second end portion and an intermediate portion connecting together the first and second end portions, the intermediate portion comprising at least three separate elongate sections arranged in side by side array each connected at each end to a respective one of the end portions of the wrap, the improvement in that the laterally outer ones of the elongate sections are longer than the central one of them.

4. The heart assist device as claimed in claim 3, wherein the laterally outer edges of the longitudinally outer ones of the elongate sections are longer than the laterally inner edges of the respective elongate sections.

5. The heart assist device as claimed in claim 4, wherein the three elongate sections each have a longitudinal axis and the axes of the two laterally outer elongate sections diverge from one another and from the central elongate section along their length from substantially a mid point of the intermediate portion to each of the end portions.

6. The heart assist device as claimed in claim 3, wherein the three elongate sections each have a longitudinal axis and the axes of the two laterally outer elongate sections diverge from one another and from the central elongate section along their length from substantially a mid point of the intermediate portion to each of the end portions.

7. In a heart assist device in which an inflatable balloon or chamber is held against an outside surface of a curved arterial vessel by a wrap formed from a flexible sheet-like material, the improvement whereby if the wrap were laid on a planar surface it would include a dome-like portion extending away from that surface.

8. The heart assist device as claimed in claim 7, wherein the dome-like shape is at least partially formed by heat setting of the sheet-like material adjacent an end of the wrap.

9. The heart assist device as claimed in claim 8, wherein the heat setting of the sheet-like material is between corresponding convexly and concavely shaped mould surfaces.

10. The heart assist device as claimed in claim 9, wherein the dome-like shape is at least partially formed by removing substantially triangular sections of the material and then joining edges of the material the adjacent removed portions.

11. The heart assist device as claimed in claim 9, wherein the dome-like shape is at least partially formed by removing substantially triangular sections of the material and then joining edges of the material the adjacent removed portions by gluing and/or suturing.

* * * * *